United States Patent
Bahammam

(10) Patent No.: US 10,842,369 B1
(45) Date of Patent: *Nov. 24, 2020

(54) STABLE DENTAL MIRROR

(71) Applicant: King Abdulaziz University, Jeddah (SA)

(72) Inventor: Laila Ahmed Bahammam, Jeddah (SA)

(73) Assignee: King Abdulaziz University, Jeddah (SA)

( * ) Notice: Subject to any disclaimer, the term of this patent is extended or adjusted under 35 U.S.C. 154(b) by 45 days.

This patent is subject to a terminal disclaimer.

(21) Appl. No.: 16/418,032

(22) Filed: May 21, 2019

(51) Int. Cl.
*A61C 5/82* (2017.01)
*A61B 1/247* (2006.01)

(52) U.S. Cl.
CPC ............... *A61B 1/247* (2013.01); *A61C 5/82* (2017.02)

(58) Field of Classification Search
CPC .................................. A61B 1/247; A61C 5/82
See application file for complete search history.

(56) References Cited

U.S. PATENT DOCUMENTS

| | | | |
|---|---|---|---|
| 659,684 A | 10/1900 | Lundborg | |
| 694,021 A | 2/1902 | Mead | |
| 1,397,090 A | 11/1921 | Dimas | |
| 4,354,835 A | 10/1982 | Lewis | |
| 5,230,622 A * | 7/1993 | Brossoit | A61B 1/0014 433/31 |
| 5,458,486 A | 10/1995 | Ballard | |
| 7,021,780 B2 | 4/2006 | Kasem | |

FOREIGN PATENT DOCUMENTS

| CN | 204562085 U | 8/2015 |
|---|---|---|
| CN | 204698501 U | 10/2015 |

\* cited by examiner

*Primary Examiner* — Ralph A Lewis
(74) *Attorney, Agent, or Firm* — Oblon, McClelland, Maier & Neustadt, L.L.P.

(57) ABSTRACT

A stable dental mirror assembly that is used by dentists during the treatment of patients is described. The mirror is fixed on a rubber dam frame that is placed in the patient's mouth during treatment. The dental mirror includes a handle on which the mirror slides. The handle includes an elbow curve. In further aspects, a method for using a dental mirror assembly and a dental mirror assembly kit are described. The dental mirror may be moved through 360 degrees and does not need to be held, thus freeing the dentist's hands. Additionally, the dental mirror assembly provides a stable visual field and allows easy movement and adjustment of the mirror.

18 Claims, 6 Drawing Sheets

Adult rubber dam frame 15 cm

STABLE DENTAL MIRROR

BACKGROUND

Technical Field

The present disclosure is directed to a dental mirror used by dentists during the treatment of patients. The mirror is fixed on the rubber dam frame that is placed in the patient's mouth during treatment. The dental mirror includes a handle on which the mirror slides. The dental mirror is able to be moved through 360 degrees and does not need to be held, thus freeing the dentist's hands.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Dentists may complain of pain in the neck, back, shoulders, and hands, in addition to stress during treatment and fatigue after the treatment, because of the need to curve over the patient for a clear field of vision.

A traditional dental mirror has a straight handle held by the dentist throughout the treatment. This mirror allows the dentist to see the teeth without bending and leaning close to the patient.

Because both hands are needed to work, the dentist must constantly change between holding the mirror and other tools or materials, which is time consuming and is stressful for the dentist. Additionally, the dentist requires constant, accurate and rapid help from the dental assistants and cannot work without an assistant.

Further, the slightest movement of the mirror during the use of a microscope or any magnifying devices may result in loss of focus of the field of operation. Readjusting the mirror may cause loss of time as well as frustration, stress and fatigue for both the dentist and patient.

U.S. Pat. No. 7,021,780 describes a dental mirror connected to a microscope, which frees the dentist's hands during treatment. The mirror has several joints that provide great freedom to guide the mirror. One drawback is that it is attached to the microscope. Any movement or vibration of the microscope or the patient's head causes the field of vision and the focus to be lost. Readjustment is difficult when higher magnification is used, as readjustment requires returning to a lower magnification to see the whole field and then adjusting to the higher magnification. This results in a loss of time and effort to restore the focus on the field. Additionally, this mirror must be attached to a dental microscope, which is expensive and not used in all dental specialties. Moreover, the mirror requires several closely spaced joints resulting in instability of the mirror, which leads to a slight vibration.

A dental mirror is described in U.S. Pat. No. 1,397,090, in which the mirror is fixed to a clamp placed on a tooth adjacent to the one to be treated. However, clamps come in many different sizes and shapes, so the mirror must be matched to the clamp size for good fit. If the correct type of the clamp is not available during treatment, this mirror cannot be used. Also, because the clamp is placed on a tooth adjacent to the one to be treated, use of a rubber dam is prevented, as a rubber dam covers all the teeth except the subject tooth, as in some specialties, such as endodontics. Further, this type of mirror cannot be used with crowded teeth or prosthetic appliances, because it cannot be placed on these teeth. If a patient has a permanent retainer attached to his teeth, it prevents placement of this mirror. Further, the presence of several joints in close proximity in this device leads to instability of the mirror yielding a slight vibration, which distorts the visual field.

U.S. Pat. No. 5,458,486 describes a mirror that can be placed on the dentist's finger. This prevents the freedom of the dentist's hands during treatment and the presence of several closely spaced joints leads to instability of the mirror yielding a slight vibration which distorts the visual field.

U.S. Pat. No. 5,230,622 describes a dental mirror placed on the high suction tip which is not always used throughout a treatment. Also, the suction tip may be constantly moved during treatment to remove moisture present around the tooth, which makes the visual stability impossible to be achieved. Thus, this invention does not provide stable visual field and does not free the dentist's hands. Again, there are closely spaced joints in the device, leading to distortion of the visual field due to vibration.

The dental mirror of the present disclosure overcomes the limitations of previous dental mirrors by placing the mirror on the rubber dam frame (RDF) used during treatment, allowing free use of either a microscope or magnifying dental loupes. The dental mirror does not have closely spaced joints, which yields good mirror stability with minimum vibration. Therefore, the mirror of the present disclosure provides a stable visual field and allows easy movement and adjustment of the mirror.

Stability of the field of vision is enhanced due to the mirror being connected to the work area, thus movement or vibration of the doctor or magnification tools does not affect the mirror and operating field. Attachment to the rubber dam frame allows the dentist's hands able to move freely once the mirror is placed.

Previous dental mirrors have complex designs with several angles and joints which makes them difficult to use during treatment and difficult to clean and sterilize after treatment. The presence of sharp angles can cause injury to the dentist, the patient or the dental assistance during a procedure or cleaning of the mirror. The dental mirror of the present disclosure is easy to use and clean because it includes one fixed piece without any sharp projections.

In an aspect, the mirror's handle is attached to RDF by a first holder which is configured to slide along the RDF allowing the dentist to position the mirror in different position within the mouth of a patient. The first holder is further configured to allow the handle to rotate within the holder and swivel with respect to the RDF. The mirror is attached to the handle by a second holder which allows the mirror to slide back and forth on the handle. The second holder is configured to allow the mirror to rotate through 360°.

SUMMARY

The present disclosure details a dental mirror assembly used by dentists during the treatment of patients. It is horizontally or vertically fixed on a conventional rubber dam frame (RDF) that is placed in the patient's mouth during treatment. In a first aspect, the assembly includes a handle, a first holder and a second holder combined with a dental mirror. The handle has a proximal end and a distal end. The handle has a curve between the proximal and distal ends. The angle of the curve may be in the range of 60 to 90 degrees. The first holder is located on the handle between the proximal end and the curve. The dental mirror is mounted by the second holder to a section of the handle between the curve and the distal end.

The handle is clipped to the RDF, which is placed in the patient's mouth during treatment, by the first holder. A clamp is placed around the patient's tooth. The first holder is a two part joint. The first part comprises a first sleeve which surrounds the handle, and a first socket radially located at the center of the first sleeve. The handle can rotate within the first sleeve to place the mirror at different locations within a patient's mouth. The second part comprises a clip which fits on the RDF and a first ball radially located at the center of the clip. The first ball and first socket fit together such that the handle can swivel with respect to the RDF and rotate through 180 degrees about the RDF.

The mirror is attached to the handle by the second holder. The second holder comprises a second sleeve which surrounds the handle. The second sleeve allows the mirror to slide along the handle between the distal end and the curve. The second sleeve further allows the mirror to rotate about the handle. The second sleeve includes a second ball radially fixed on the second sleeve. The mirror has a back plate which comprises a second socket. The second ball of the second sleeve is configured to fit within the second socket so as to allow the mirror to swivel and rotate with respect to the handle.

In an aspect, the proximal end of the handle may include a grip to prevent slippage of the fingers in the wet environment of the mouth. The grip may be any of a textured section, a shaped section, or a slip-on end cap or sleeve.

In a further aspect, a method for using a dental mirror assembly comprises clipping, by a first holder, a handle to a rubber dam frame; attaching a mirror to the handle by a second holder; adjusting the position of the mirror by moving the handle within the first holder and moving the mirror within the second holder.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
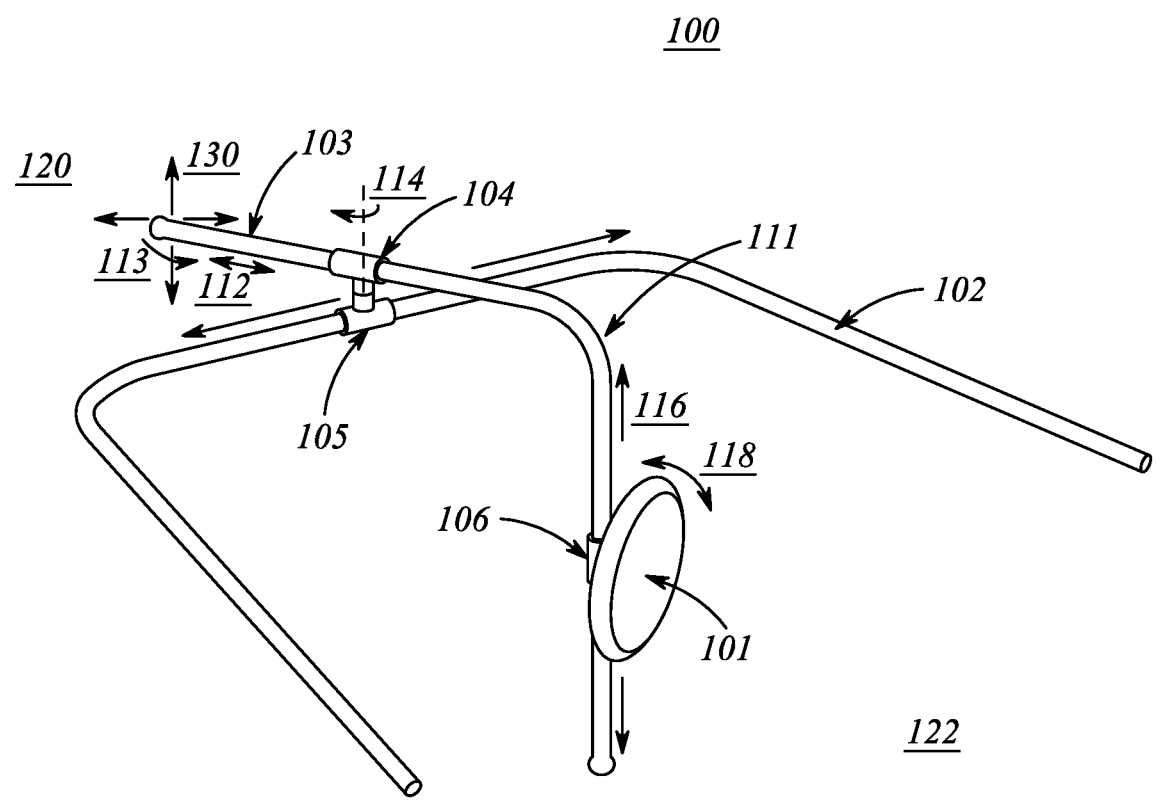
FIG. 1A illustrates the mirror attached to the rubber dam frame, according to certain embodiments.

In the drawings, like reference numerals designate identical or corresponding parts throughout the several views.

Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

Aspects of this disclosure are directed to a dental mirror assembly, a method for using a dental mirror assembly and a method for assembling a dental mirror kit.

An overview of the dental mirror assembly of the present disclosure is given below. The present disclosure relates to a stable dental mirror which fixes to a rubber dam frame 102 (RDF) as shown in FIG. 1A-1E and FIGS. 2-4.

Figure 2:
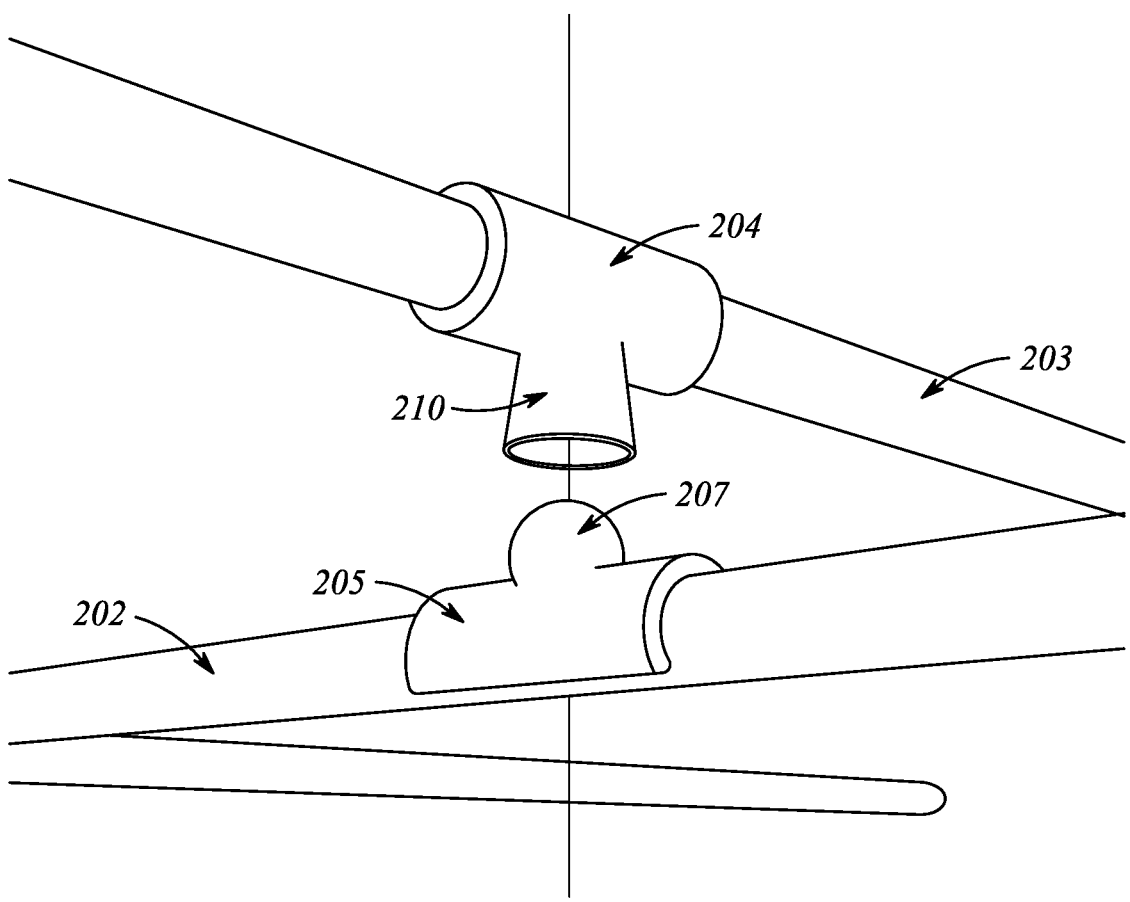
FIG. 2 illustrates the way in which the mirror is fitted on the rubber dam frame and the joint that facilitates the movement of the handle, according to certain embodiments.

A holder 105 connects handle 103 to the RDF 102, wherein the holder 105 is configured to allow the handle to be moved laterally (proximally or distally) along the rubber dam frame 102 to adjust the mirror position within a patient's mouth. As shown in FIG. 2, the holder 205 includes a ball 207, which fits within a socket 210 of a corresponding sleeve 204 which holds the handle. The combination of ball 207 and socket 210 allow a dentist to adjust the position of the distal end of the handle by rotating and/or swivelling the ball within the socket. The sleeve 204 is configured to allow movement of the handle along the longitudinal axis of the sleeve, in order to adjust the depth that the distal end of the handle is inserted into the patient's mouth.

Figure 4:
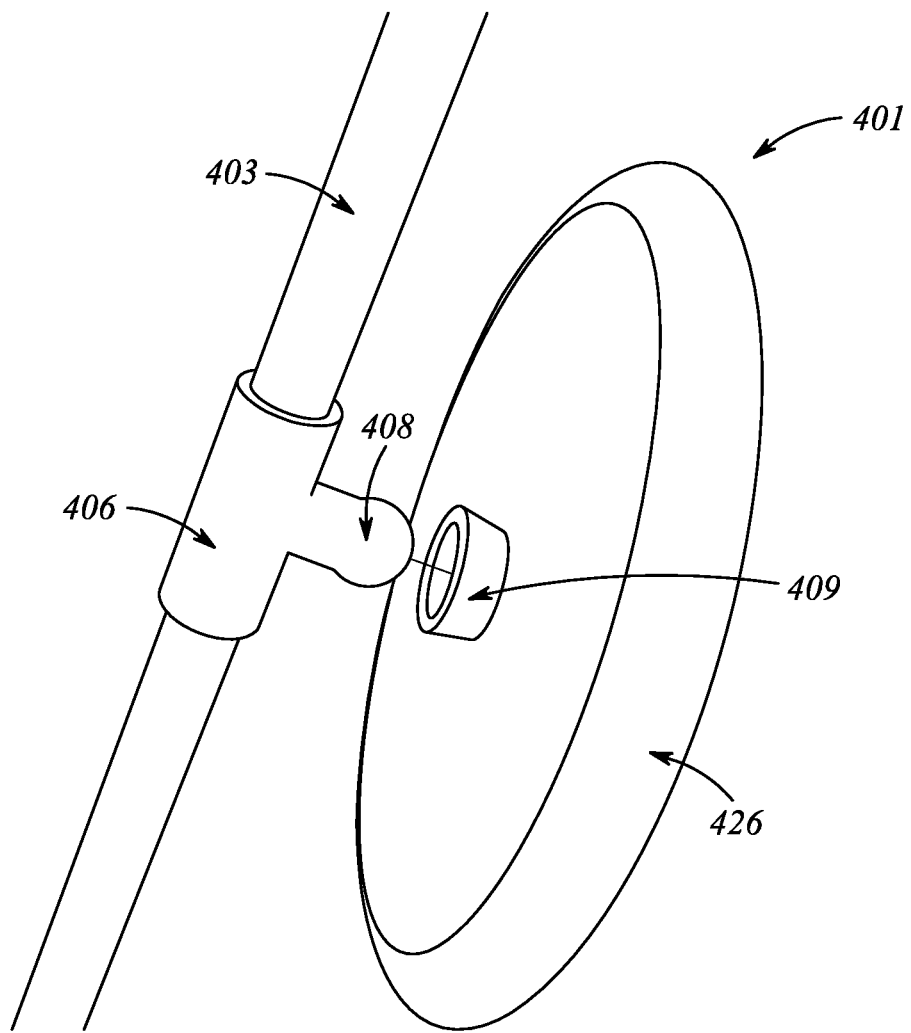
FIG. 4 illustrates the ball and socket joint which enables circular and swivel movement of the mirror on the handle, according to certain embodiments.

The dental mirror assembly has a handle 103 with a 60-90 degree (elbow) curve 111 in the middle, where the handle is connected to a support structure (RDF) 102. The handle is inserted into a second holder (106, 406) having a ball 408 which is inserted in a socket 409 on the back of mirror (101, 401), as shown in FIGS. 1A and 4. The ball and socket combination allows 360 degree rotation of the mirror with respect to the handle and allows the mirror to swivel or tilt about the holder. The sleeve 106 is configured to move along a straight section of the handle 103 between the distal end of the handle 103 and the angle 111.

Figure 1C:
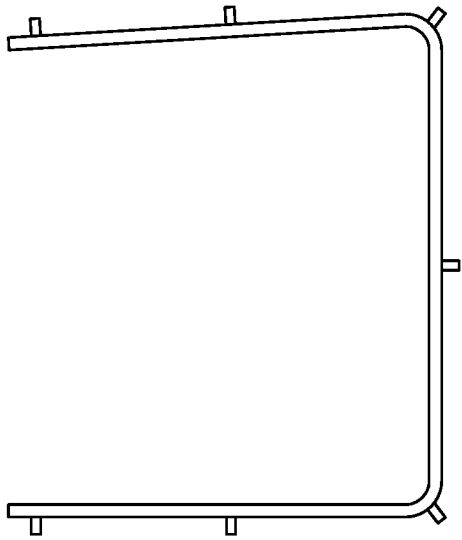
FIG. 1B-1D illustrate types of rubber dam frames which may be used with the stable dental mirror.
Figure 1D:
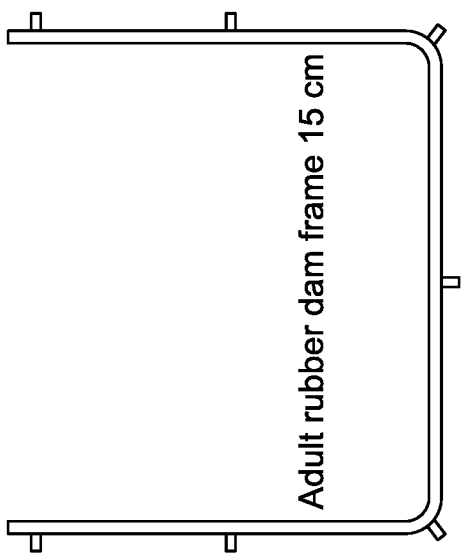
Figure 1B:
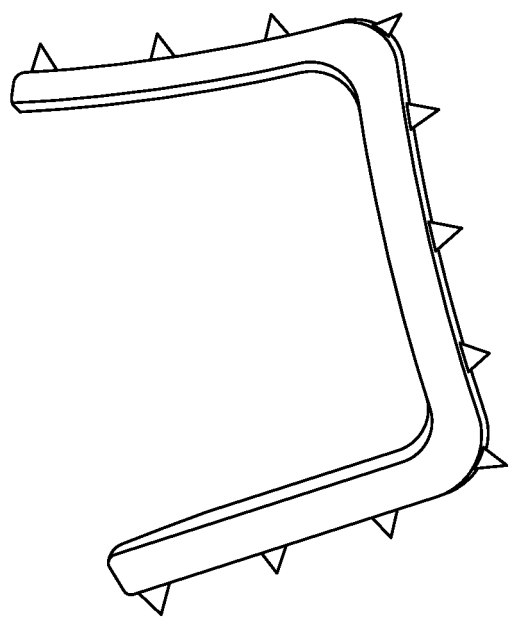
Figure 1E:
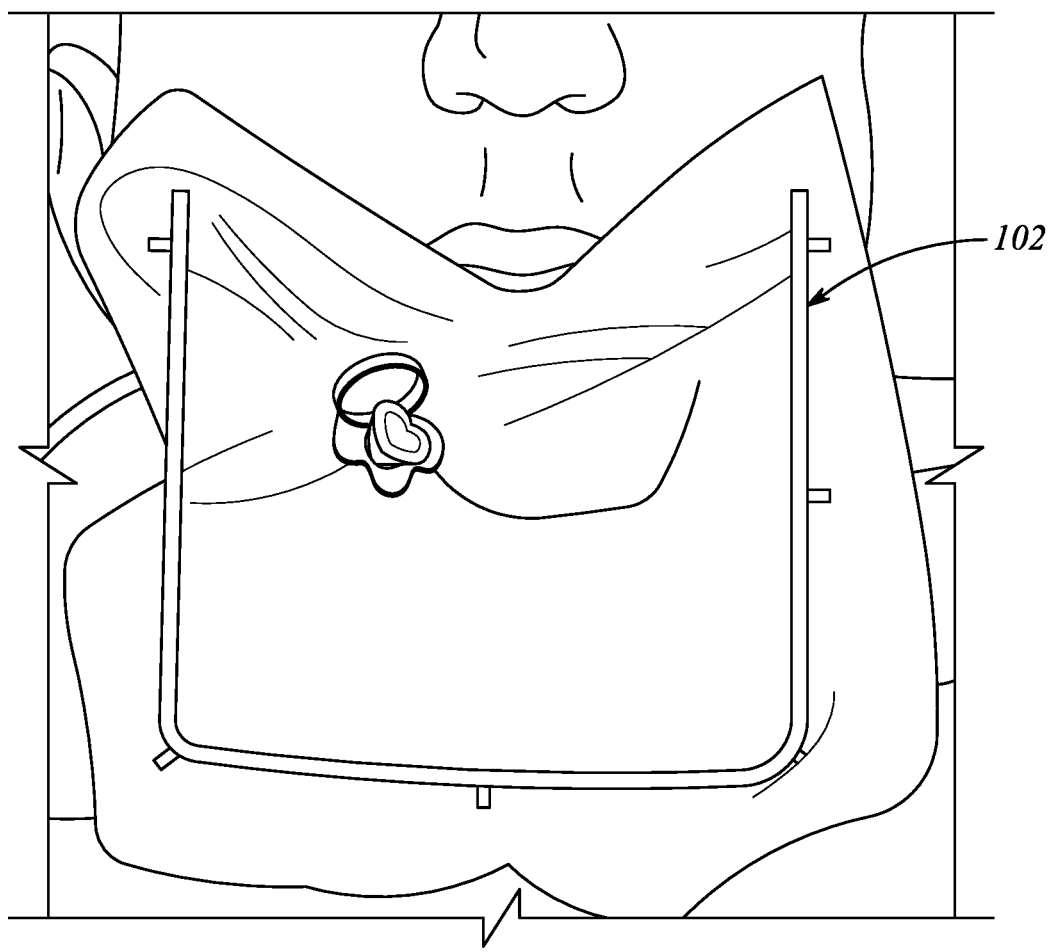
FIG. 1E illustrates the way in which the rubber dam and rubber dam frame are used to protect the patient's mouth.

The dental mirror assembly consists of one piece separate from RDF. After the application of the RDF, the mirror is attached to any side of the RDF by a holder. The RDF (see FIG. 1B-1D) is used to hold the mirror and a rubber dam sheet. The dental mirror would be attached to the rubber dam frame at a position which gives a good visual image of a tooth exposed through a hole in the rubber dam sheet. FIG. 1E illustrates the rubber dam frame and rubber dam sheet inserted in a patient's mouth to isolate the tooth from the mouth.

The ball/socket attachments allow 360 degree movement of the mirror and 180 degrees movement of the handle.

In a non-limiting example, the handle may be about 12 cm long with a curve at the middle. The curve is 60-90 degrees, preferably 70-80 degrees, even more preferably 75 degrees.

In a non-limiting example, the rubber dam frame may be a 4 inch rubber dam frame, such as is sold by ProDent USA, part number 30-274, Net32 Inc., 250 Towne Village Dr., Cary, N.C. 27513, USA, world wide web.net32. com/ec/prodent-usa-4-rubber-dam-frame-d-24858?utm_source=Windfall&utm_medium=product feed&utm_content=dental&utm_campaign=googles hopping&utm_source=google&utm_medium=cpc& adpos=1o5& scid=scp1p1248 58& sc_intid=124858&gclid=EAIaIQobChMIj9yIqomA4 QIViVuGCh0FfAu2EAQYBSABE gli4fD_BwE. Different types of rubber dam frames are illustrated in FIG. 1B-1D. The frame may be made of stainless steel or plastic.

The handle may be manufactured using metal or plastic materials, preferably stainless steel. The handle can be made of any type of materials such as a metal (as stainless steel), plastic (that accommodate high sterilization temperature if not disposable) or a combination. Further, the handle may be manufactured to have an adjustable bend, and may include such features as a spring and clip to retain the bend, an articulated handle, a handle made of shape memory material, or such like.

The mirror can be made of any type of materials; metals, plastics (that accommodate high sterilization temperature if not disposable) or a combination of both. The mirror can be used as a disposable instrument which can be made of an inexpensive plastic material. The mirror is a single piece, which is preassembled such that parts 401, 403, 406, 408 and 409 as shown in FIG. 4 are one piece.

A first embodiment is shown in FIGS. 1A-1E and 2-4. The first embodiment is drawn to a dental mirror assembly 100, comprising a handle 103 having a longitudinal axis, a proximal end 120 and a distal end 122, the handle having an elbow curve 111 between the proximal and the distal ends, a dental mirror 101, a rubber dam frame 102 (RDF). The assembly includes a first holder 105 attached to the handle and the rubber dam frame between the proximal end 120 and the curve 111. A second holder 106 is attached to the handle and the dental mirror 101 between the curve 111 and the distal end 122.

As shown in detail in FIG. 2, the first holder 205 includes a first sleeve 204 configured to surround the handle 203, wherein the first sleeve includes a first socket 210 located radially outwardly at the center of the first sleeve. The first holder includes a clip configured to at least partially surround the rubber dam frame as shown in FIG. 2, wherein the clip includes a first ball 207 radially located at the center of the clip.

The first socket 210 and the first ball 207 are configured to fit together such that the handle may rotate (see 114, FIG. 1A) through 180 degrees and swivel (see 130, FIG. 1A) with respect to the RDF 202.

The first sleeve 204 is configured such that the handle can move laterally (see 112, FIG. 1A) between the proximal end 120 and the curve 111 and so that the handle may be rotated (see 113, FIG. 1A) through 360 degrees about the axis of the handle within the first sleeve.

The dental mirror 101 comprises a mirror frame (326, 426) and a mirrored surface (FIG. 1A, 3, 4), wherein the mirrored surface is held within the mirror frame. The mirror frame 326 includes a socket 309 opposite to and radially extending away from the mirrored surface.

Figure 3:
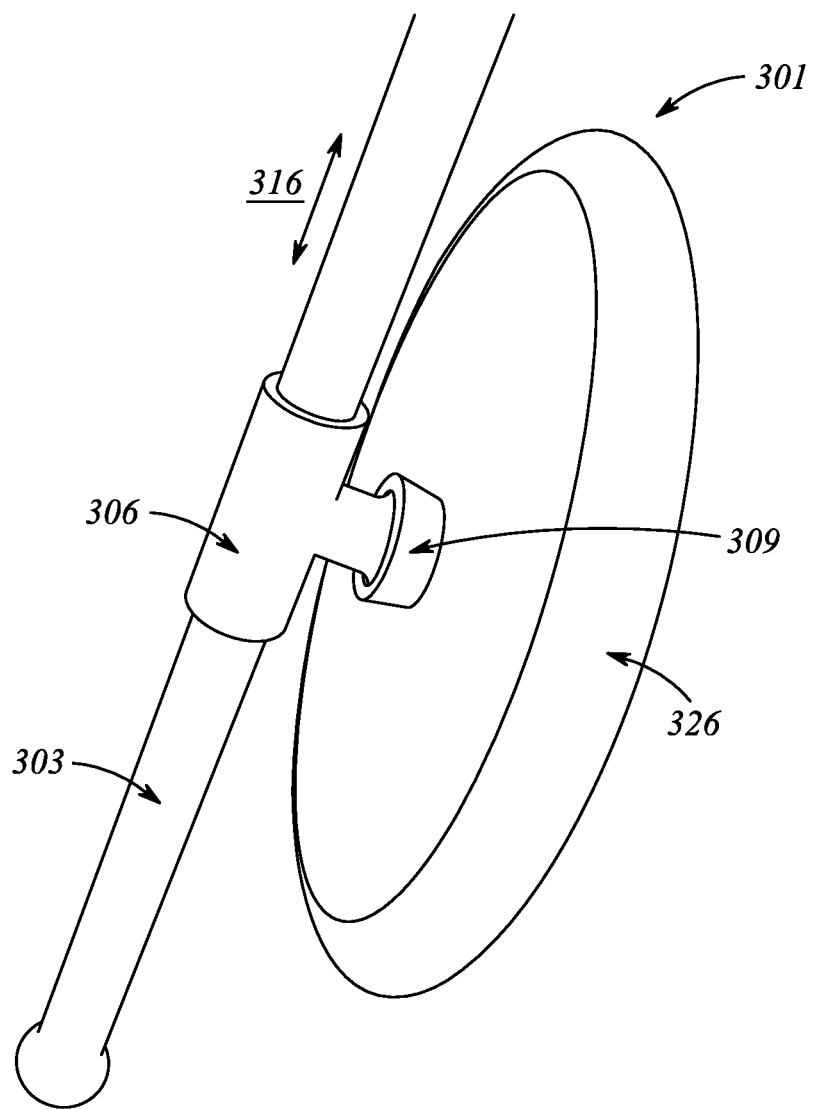
FIG. 3 illustrates lateral movement of the mirror on the handle, according to certain embodiments.

The second holder 406 includes a ball end 408, wherein the ball end forms a rotatable (see 118, FIG. 1A) and swivelable attachment with the ball inserted in the socket. FIG. 3 shows the ball inserted in the socket and FIG. 4 shows the ball and socket before insertion.

The second holder 406 includes a second sleeve configured to surround the handle 403, wherein the second sleeve includes the second ball 408 radially located at the center of the second sleeve. The second sleeve is configured such that the mirror can slide (see 116, FIG. 1A) between the curve 111 and the distal end 122; and wherein the second sleeve is further configured such that the mirror may be rotated (see 118, FIG. 1A) through 360 degrees with respect to the axis of the handle.

The angle of the curve is in the range of 60-90 degrees, preferably 70-80 degrees, even more preferably 75 degrees.

The handle 103 has a length defined by the distance between the proximal 120 and distal ends 122, and wherein the curve is located along the length at a distance between ¼ to ⅔ of the length, preferably ⅓ to ⅔ of the length, more preferably ⅝ to ⅞ of the length, even more preferably ½ of the length.

The handle may have rounded proximal and distal ends to prevent tearing of the soft tissues of a patient's mouth, such as lips or cheeks, the rubber dam sheet or the dentist's gloves and hands.

The proximal end of the handle may include a gripping surface, wherein the gripping surface is selected from the group comprising a surface roughness, a coating, an end cap, a patterned surface, a shaped end, and a gripping sleeve.

In a non-limiting example, a soft mirror grip may be used such as the Disposable Dental Mirror Grip manufactured by Magnificent Medical Equipment, 222 Merchandise Mart Plaza Ste. 1230, Chicago, Ill. 60654, world wide web. softdentalgrips.com/mirror-grips.

The surface roughness may be at least one of a stippling, a grating, an indentation and a raised area; the coating is a non-slip coating; the end cap is at least one of a hard end cap and a soft end cap, wherein a hard end cap is shaped to have a gripping area and a soft end cap is configured to depress when gripped; the patterned surface includes a finger shaped indentation; the shaped end includes one of a square end, a round end, a flat end, a crossbar, a round end with at least one flat surface and a finger shaped indentation; and the gripping sleeve is one of a rough plastic sleeve, a soft plastic sleeve, a foam sleeve, a leather sleeve and a metal sleeve.

The handle may be made of plastic, the first and second holders are made of nylon, and the mirror frame may be made of metal. The mirror may be made of one piece, such that the second holder and mirror frame are made of inexpensive plastic or stainless steel.

The handle may constructed of flexible material such that the angle of the curve is adjustable. For example, the handle may be made of nickel titanium, which has the property of shape memory. Alternatively, the handle may be non-adjustable.

The second embodiment is shown in FIGS. 1A-1E and 2-4. The second embodiment is drawn to a method for using a dental mirror assembly comprising clipping, by a clip configured to at least partially surround a rubber dam frame 102, a first holder 105 to the rubber dam frame and connecting the first holder to a proximal end 120 of a handle 103, wherein the handle has a bend 111 between the proximal end 120 and a distal end 122; attaching a mirror 101 to the distal end of the handle by a second holder 106; adjusting the position of the mirror by moving the handle within the first holder and moving the mirror within the second holder.

As shown in FIG. 2, the method further comprises connecting the first holder to the handle by inserting the proximal end 120 of the handle into a first sleeve 204 of the first holder, the first sleeve including a first socket 210 radially located at the center of the sleeve 204; inserting a first ball 207 radially located at the center of the clip into the first socket 210. The method includes adjusting the position of the mirror by at least one of sliding the handle within the first sleeve, rotating the handle within the first sleeve, swiveling the ball within the socket, and rotating the socket with respect to the rubber dam frame.

Attaching the mirror to the handle is accomplished by connecting the second holder 106 to the mirror 101 by inserting the distal end 122 of the handle 103 into a second sleeve of the second holder 106, as shown in FIG. 3, 4, and inserting a second ball 408, the second ball radially located at the center of the second sleeve, into a second socket 409 attached to a back side of a frame 426 surrounding the mirror 401. The method includes adjusting the position of the mirror on the handle by at least one of sliding the handle within the second sleeve, rotating the mirror around the handle, and swiveling the ball within the socket. In a non-limiting example, the length of the mirror is about 12 min.

The method further comprises adjusting the bend of the handle by bending the handle, wherein an angle of the bend is in the range of 50-90 degrees, preferably 70-80 degrees, even more preferably 75 degrees, and adjusting the bend of the handle along its length by bending the handle at a distance between ¼ to ⅔ of the length, preferably ⅓ to ⅔ of the length, more preferably ⅝ to ⅞ of the length, even more preferably ½ of the length.

The third embodiment is shown with respect to FIG. 1A-1E and FIG. 3-4. The third embodiment describes a method for assembling a dental mirror kit, comprising providing a rubber dam frame 102, a two part holder 205 including a first part having a first sleeve 104 and a first socket 210 radially located outwardly from the center of the first sleeve and a second part having a gripping clip and a first ball 207 radially located outwardly from the center of the gripping clip. The handle is attached to the rubber dam frame by inserting a first end of a handle into the first sleeve and inserting the first ball into the first socket.

The method of assembling continues by providing a mirror 101 having a mirrored surface, inserting the mirror 401 into a frame 426, wherein the frame has a back side opposite the mirrored surface, the back side of the frame including a second socket 409 radially extending away from the mirrored surface. Thereupon, insetting the distal end 122 of the handle 103 into a second sleeve, the second sleeve including a ball 408 extending radially outwardly from the center of the second sleeve; and inserting the second ball into the second socket. As mentioned above, the mirror and second holder may be preassembled.

Assembling a dental mirror kit, further comprises sliding a gripping sleeve (not shown) over the proximal end 120 of the handle, wherein the gripping sleeve is one of a rough plastic sleeve, a soft plastic sleeve, a foam sleeve, a leather sleeve and a metal sleeve.

This dental mirror assembly is used by dentists who use the rubber dam during their dental treatment to keep both dentist's hands free to use during treatment and fix the visual field during magnification.

The dental mirror assembly may further include a light attached to a third holder near the dental mirror. Alternatively, the dental mirror may include a lighted ting or a lighted area on the frame of the mirror.

The dental mirror assembly is not limited by the materials suggested above, and can be manufactured from any metal, plastic material (whether disposable or not) or any other mixture of both materials suitable for the purpose for which the invention is designed, and the materials involved in the manufacture of the assembly do not limit the method of using the assembly.

Obviously, numerous modifications and variations of the present invention are possible in light of the above teachings. It is therefore to be understood that within the scope of the appended claims, the invention may be practiced otherwise than as specifically described herein.

The invention claimed is:

1. A dental mirror assembly, comprising:
    a handle having a longitudinal axis, a proximal end and a distal end, the handle having a curve between the proximal and the distal ends;
    a dental mirror;
    a rubber dam frame (RDF);
    a first holder attached to the handle and the rubber dam frame between the proximal end and the curve;
    a second holder attached to the handle and the dental mirror between the curve and the distal end,
    wherein the first holder includes a first sleeve configured to surround the handle, wherein the first sleeve includes a first socket radially located at the center of the first sleeve;
    wherein the first holder further includes a clip configured to at least partially surround the rubber dam frame, wherein the clip includes a first ball radially located at the center of the clip; and
    wherein the first socket and the first ball are configured to fit together such that the handle may rotate through 180 degrees and swivel with respect to the RDF.

2. The dental mirror assembly of claim 1,
    wherein the first sleeve is configured such that the handle can move laterally between the proximal end and the curve; and
    wherein the first sleeve is further configured such that the handle may be rotated through 360 degrees about the axis of the handle within the first sleeve.

3. The dental mirror assembly of claim 1,
    wherein the dental mirror further comprises a mirror frame and a mirrored surface, wherein the mirrored surface is held within the mirror frame;
    wherein the mirror frame includes a socket opposite to and radially extending away from the mirrored surface.

4. The dental mirror assembly of claim 3, wherein the second holder includes a ball end, wherein the ball end forms a rotatable and swivelable attachment with the socket when the ball is inserted within the socket.

5. The dental mirror assembly of claim 1,
    wherein the second holder includes a second sleeve configured to surround the handle, wherein the second sleeve includes a second ball radially located at the center of the second sleeve;
    wherein the mirror comprises a frame having a second socket;
    wherein the second ball and the second socket are configured to fit together such that the mirror may swivel with respect to the handle.

6. The dental mirror assembly of claim 5,
    wherein the second sleeve is configured such that the mirror can slide between the curve and the distal end; and
    wherein the second sleeve is further configured such that the mirror may be rotated through 360 degrees with respect to the axis of the handle.

7. The dental mirror assembly of claim 1, wherein the angle of the curve is in the range of 50-90 degrees.

8. The dental mirror assembly of claim 1,
    wherein the handle has a length defined by the distance between the proximal and distal ends, and wherein the curve is located along the length at a distance between ¼ to ⅔ of the length.

9. The dental mirror assembly of claim 1, wherein the handle has rounded proximal and distal ends.

10. The dental mirror assembly of claim 1, wherein the proximal end of the handle includes a gripping surface, wherein the gripping surface is selected from the group consisting of a surface roughness, a coating, an end cap, a patterned surface, a shaped end, and a gripping sleeve;
  wherein the surface roughness is at least one of a stippling, a grating, an indentation and a raised area;
  wherein the coating is a non-slip coating;
  wherein the end cap is at least one of a hard end cap and a soft end cap, wherein a hard end cap is shaped to have a gripping area and a soft end cap is configured to depress when gripped;
  wherein the patterned surface includes a finger shaped indentation;
  wherein the shaped end includes one of a square end, a round end, a flat end, a crossbar, a round end with at least one flat surface and a finger shaped indentation; and
  wherein the gripping sleeve is one of a rough plastic sleeve, a soft plastic sleeve, a foam sleeve, a leather sleeve and a metal sleeve.

11. The dental mirror assembly of claim 1, wherein the handle is made of plastic, and the first and second holders are made of nylon.

12. The dental mirror assembly of claim 1, wherein the handle is constructed of flexible material such that the angle of the curve is adjustable.

13. A method for using the dental mirror assembly of claim 1, comprising:
  clipping, by the clip, the first holder to the rubber dam frame and connecting the first holder to the proximal end of the handle
  attaching the dental mirror to the distal end of the handle by the second holder;
  adjusting the position of the dental mirror by moving the handle within the first holder and moving the mirror within the second holder.

14. The method for using a dental mirror assembly of claim 13, further comprising
  connecting the first holder to the handle by inserting the proximal end of the handle into the first sleeve of the first holder, the first sleeve including the first;
  inserting the first ball into the first socket;
  adjusting the position of the dental mirror by at least one of sliding the handle within the first sleeve, rotating the handle within the first sleeve, swiveling the ball within the socket, and rotating the socket with respect to the rubber dam frame.

15. The method for using a dental mirror assembly of claim 13, further comprising adjusting the bend of the handle by bending the handle, wherein an angle of the bend is in the range of 50-90 degrees.

16. The method for using a dental mirror assembly of claim 13, further comprising
  adjusting the bend of the handle along its length by bending the handle at a distance between ¼ to ⅔ of the length.

17. A method for assembling a dental mirror kit, comprising:
  providing a rubber dam frame;
  providing a two part holder including a first part having a first sleeve and a first socket radially located outwardly from the center of the first sleeve and a second part having a gripping clip and a first ball radially located outwardly from the center of the gripping clip;
  inserting a first end of a handle into the first sleeve;
  inserting the first ball into the first socket;
  providing a mirror having a mirrored surface;
  inserting the mirror into a frame, wherein the frame has a back side opposite the mirrored surface, the back side of the frame including a second socket radially extending away from the mirrored surface;
  inserting the distal end of the handle into a second sleeve, the second sleeve including a ball extending radially outwardly from the center of the second sleeve; and
  inserting the second ball into the second socket.

18. The method for assembling a dental mirror kit of claim 17, further comprising:
  sliding a gripping sleeve over the proximal end of the handle, wherein the gripping sleeve is one of a rough plastic sleeve, a soft plastic sleeve, a foam sleeve, a leather sleeve and a metal sleeve.

* * * * *